United States Patent [19]

Sommer et al.

[11] 4,250,107

[45] Feb. 10, 1981

[54] N-(SULFOALKANE) AMINO ALKANE PHOSPHONIC ACIDS AND THEIR WATER-SOLUBLE SALTS

[75] Inventors: Klaus Sommer, Heidelberg; Gottfried Schoebel, Ludwigshafen, both of Fed. Rep. of Germany

[73] Assignee: Benckiser-Knapsack GmbH, Ladenburg, Fed. Rep. of Germany

[21] Appl. No.: 958,188

[22] Filed: Nov. 6, 1978

[30] Foreign Application Priority Data

Dec. 27, 1977 [DE] Fed. Rep. of Germany ....... 2758306

[51] Int. Cl.³ ............................ C07F 9/38; C02B 5/06; D06M 9/08
[52] U.S. Cl. ................................. 260/502.5; 210/700; 252/8.8; 252/180
[58] Field of Search ....................................... 260/502.5

[56] References Cited

U.S. PATENT DOCUMENTS

| | | | |
|---|---|---|---|
| 2,673,213 | 3/1954 | Bersworth | 260/502.5 |
| 2,836,620 | 5/1958 | Bersworth et al. | 260/502.5 |
| 3,190,907 | 6/1965 | Distler et al. | 260/513 N |
| 4,006,182 | 2/1977 | Pluger et al. | 260/502.5 |
| 4,085,134 | 4/1978 | Redmore et al. | 260/502.5 |

FOREIGN PATENT DOCUMENTS

| | | |
|---|---|---|
| 2713827 | 10/1978 | Fed. Rep. of Germany. |
| 2716417 | 10/1978 | Fed. Rep. of Germany. |
| 1435744 | 5/1976 | United Kingdom. |
| 513981 | 10/1976 | U.S.S.R. .............. 260/502.5 |

OTHER PUBLICATIONS

Kirk–Othmer Encyclopedia of Chemical Technology, 2nd ed; Interscience (1969) vol. 19, pp. 290–291.

*Primary Examiner*—Joseph E. Evans
*Attorney, Agent, or Firm*—Schwartz, Jeffery, Schwaab, Mack, Blumenthal & Koch

[57] ABSTRACT

N-(sulfo alkane) amino alkane phosphonic acids or their water-soluble salts are obtained by reacting an alkali metal salt of an amino alkane phosphonic acid with at least one hydrogen atom in the amino group which can be replaced by a sulfo alkane group, in an alkaline medium with an alkane sultone while heating.

9 Claims, No Drawings

N-(SULFOALKANE) AMINO ALKANE PHOSPHONIC ACIDS AND THEIR WATER-SOLUBLE SALTS

CROSS REFERENCE TO RELATED APPLICATION

The present application is related to U.S. patent application Ser. No. 891,043 of KLAUS SOMMER and HERMANN WEBER, filed Mar. 28, 1978 and entitled "N-SULFO ALKANE AMINO ALKANE PHOSPHONIC ACIDS AND THEIR ALKALI METAL SALTS AND A PROCESS OF PRODUCING SAME" and to Application Ser. No. 891,143 of KLAUS SOMMER, HERMANN WEBER, AND WILHELM SPATZ filed Mar. 28, 1978 and entitled "PROCESS OF PRODUCING N-SULFO ALKANE AMINO ALKANE PHOSPHONIC ACIDS AND THEIR ALKALI METAL SALTS" now abandoned.

BACKGROUND OF THE INVENTION

1. Field of the Invention

The present invention relates to a novel, advantageous, and economic process of producing N-sulfo alkane amino alkane phosphonic acids and their water-soluble salts, to novel compounds obtained by said process, to compositions containing same, and to methods of using such compositions.

2. Description of the Prior Art

U.S. patent application Ser. No. 891,043 of KLAUS SOMMER and HERMANN WEBER discloses novel and highly advantageous N-sulfo alkane amino alkane phosphonic acids and their water-soluble salts. According to said application, such compounds are prepared by reacting an alkali metal salt of an amino alkane phosphonic acid in an alkaline solution with an alkali metal salt of a halogen or hydroxy substituted alkane sulfonic acid in a molar proportion between about 1:1 and about 1:2 of phosphonic acid reactant to sulfonic acid reactant, while heating. To carry out this process it is usually necessary to heat the reaction mixture to boiling under pressure at a temperature between about 180° C. and about 240° C.

SUMMARY OF THE INVENTION

It is one object of the present invention to provide a simple, effective, and economic process of producing N-sulfo alkane amino alkane phosphonic acids and their water-soluble salts which process does not require heating to temperatures of 100° C. and even higher.

Another object of the present invention is to provide novel and highly advantageous N-sulfo alkane amino alkane phosphonic acids and their water-soluble salts.

A further object of the present invention is to provide compositions containing novel N-sulfo alkane amino alkane phosphonic acids and their water-soluble salts.

Still another object of the present invention is to provide a method of using novel N-sulfo alkane amino alkane phosphonic acids and their water-soluble salts as sequestering agents which form complex compounds with bivalent and polyvalent metal ions so that they are useful in all instances in which effective complex-forming ability is required.

In principle, the novel and advantageous process according to the present invention comprises the step of reacting alkali metal salts of amino alkane phosphonic acids of the following formula

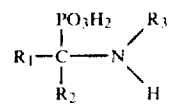

in which $R_1$ indicates hydrogen, alkyl with 1 to 11 carbon atoms, especially methyl or ethyl, aryl, especially phenyl, tolyl, or chloro phenyl, aralkyl, especially benzyl, cycloalkyl, especially cyclohexyl, amino alkylene with 2 to 5 carbon atoms, especially amino methylene $CH_2NH_2$, hydroxy alkylene, especially hydroxy methylene $CH_2OH$ or hydroxy ethylene $C_2H_4OH$, carboxy alkylene, especially carboxy methylene $CH_2.COOH$, or a lower alkylene phosphonic acid group, especially the ethylene phosphonic acid group $C_2H_4.PO_3H_2$;

$R_2$ indicates hydrogen or the phosphonic acid group $PO_3H_2$; and $R_3$ indicates hydrogen methyl, or a lower alkylene phosphonic acid group, especially the methylene phosphonic acid group $CH_2.PO_3H_2$ in an alkaline medium with an inner ester of a hydroxy alkane sulfonic acid, i.e. a sultone of the formula

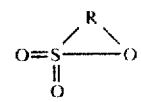

in which

R indicates alkyl with 3 to 20 carbon atoms.
Preferred sultones of this type are the following:
1,3-Propane sultone,
1,3-butane sultone,
1,4-butane sultone,
1,3-hexane sultone,
1,3-dodecane sultone,
1,3-heptadecane sultone,
1,4-tetradecane sultone,
3-methyl-2,4-heptane sultone,
2,2-dimethyl-1,3-hexane sultone,
2,5-hexane sultone
and the like sultones.

In general, any amino alkane phosphonic acids which contain at the amino group at least one hydrogen atom capable of being substituted by a sulfo alkane group and which correspond to the above given formula have proved to be suitable phosphonic acid reactants. Preferred reactants are, for instance, the sodium or potassium salts of the following amino alkane phosphonic acids:

Amino methane phosphonic acid,
amino methane diphosphonic acid,
N-methyl amino methane diphosphonic acid,
imino-bis-(methane phosphonic acid),
1-amino ethane-1,1-diphosphonic acid,
1-amino propane-1,1-diphosphonic acid,
phenyl amino methane diphosphonic acid,
2-carboxy-1-amino ethane-1,1-diphosphonic acid,
1-amino propane-1,1,3-triphosphonic acid,
1,2-di-amino ethane-1,1-diphosphonic acid,
3-hydroxy-1-amino propane-1,1-diphosphonic acid,
1-hydroxy-3-amino propane-1,1-diphosphonic acid,
and the like phosphonic acids.

The process according to the present invention has the advantage over the processes disclosed in Patent Application Serial No. 891,043 that the sultones react quite readily with the amino phosphonic acids according to the following reaction equations whereby the sultone ring is split up:

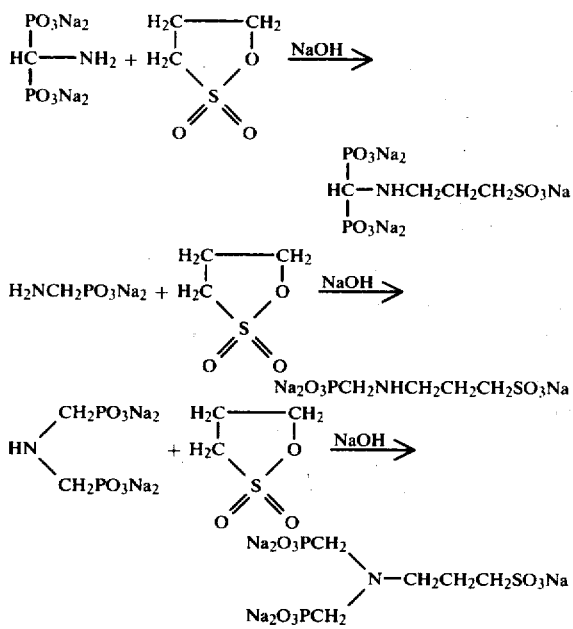

Of course, in place of the amino methane mono- and diphosphonic acids and the amino bis(methane phosphonic acid) and of the 1,3-propane sultone, there can be used other amino alkane phosphonic acids and alkane sultones.

The reaction is preferably carried out by dissolving the amino alkane phosphonic acid in an alkaline medium, the pH-value of which is at least 9.0 and preferably between 10.0 and 12.0, and adding drop by drop thereto the respective alkane sultone. Thereafter, the reaction mixture is heated at a temperature which is below 100° C., preferably at a temperature between about 60° C. and about 90° C. for about one hour to two hours so as to achieve complete reaction.

The novel phosphonic acid compounds according to the present invention are excellent complexing or sequestering agents with respect to bivalent or polyvalent metal ions. Thus they can be employed with advantage in all those instances where a complexing or sequestering power is required. More particularly, the novel compounds excel by their high resistance to hydrolysis even at a high temperature. Due thereto they can be employed in all aqueous media in which temperatures exceeding 100° C. are encountered and in which the hardness causing agents present therein cause trouble or in which the effect of polyvalent metal ions is to be excluded. More particularly they have proved to be useful, as stated above, for softening hard water, as additives to textile treatment baths, in paper manufacture, in tanning baths, and for other purposes.

The novel phosphonic acid compounds are also useful for stabilizing the hardness of water when added in substoichiometric amounts, i.e. for carrying out the so-called "threshold processes."

The novel phosphonic acid compounds according to the present invention combine the properties of compounds which contain sulfonic acid groups with the properties of compounds containing amino groups. Especially advantageous is the exceedingly high solubility of the free acids in aqueous media, a property which most of the heretofore known amino phosphonic acids do not possess. Thus at least amounts of 100 g. of the compounds described hereinafter in the examples are soluble in 100 cc. of aqueous medium.

DESCRIPTION OF THE PREFERRED EMBODIMENTS

The following examples serve to illustrate the present invention without, however, being limited thereto.

EXAMPLE 1

47.8 g. of amino methane diphosphonic acid are dissolved with 70 g. of potassium hydroxide in 200 cc. of water while stirring vigorously. 32 g. of 1,3-propane sultone, dissolved in 75 cc. of ethanol or isopropanol, are added drop by drop thereto at a temperature between 40° C. and 50° C. while continuing vigorous stirring. Thereupon, the reaction mixture is heated at 80° C. to 90° C. for one hour. After cooling, the reaction solution is adjusted to slightly acid reaction by the addition of hydrochloric acid. Any precipitated unreacted amino methane diphosphonic acid is removed by filtration. The filtered solution is treated with a cation exchange agent. After evaporating the treated solution to dryness and washing the residue with ethanol, the N-(sulfo propane) amino methane diphosphonic acid is obtained. Said acid is contaminated by a small amount of N-bis-(sulfo propane) amino methane diphosphonic acid. The yield is 89.5% of the theoretical yield. The acid exhibits a lime-binding power of 25 g. of Ca for 100 g. of acid.

Analysis:
Found: C: 15.6%, N: 4.1%, P: 19.1%, S: 10.9% Calculated: C: 15.34%, N: 4.47%, P: 19.78%, S: 10.24%.

EXAMPLE 2

47.8 g. of amino methane diphosphonic acid, 84 g. of potassium hydroxide, and 64 g. of 1,3-propane sultone are reacted in 100 cc. of ethanol as described hereinabove in Example 1. Thereby, 112 g. of N,N-bis-(sulfo propane) amino methane diphosphonic acid are obtained. The acid has a lime-binding power of 18.5 g. Ca for 100 g. of acid. Yield: 93.5% of the theoretical yield.

Analysis:
Found: N: 3.5%, P: 14.6%, S: 14.8%. Calculated: N, 3.22%, P: 14.23%, S: 14.73%.

EXAMPLE 3

47.8 g. of amino methane diphosphonic acid are suspended in 150 cc. of water. 140 g. of a 50% potassium hydroxide solution are added drop by drop thereto. Thereafter, a solution of 36 g. of 1,3-butane sultone in 75 cc. of ethanol are added drop by drop thereto while stirring vigorously. The reaction mixture is worked up as described in Example 1 and yields N-(sulfo butane) amino methane diphosphonic acid.

Yield: 91.5%.
Analysis:
Found: N: 4.0%, P: 18.1%, S: 10.5%. Calculated: N: 4.28%, P: 18.93%, S: 9.79%.

EXAMPLE 4

The procedure is the same as described in Example 3 whereby, however, 36 g. of 1,4-butane sultone are used as sultone reactant. N-(sulfo butane) amino methane diphosphonic acid is obtained in a yield of 86.3% of the theoretical yield.

EXAMPLE 5

51. g. of 1-amino ethane-1,1-diphosphonic acid are dissolved together with 50 g. of sodium hydroxide in 40 cc. of water. 45 g. of 1.3-hexane sultone dissolved in 80 cc. of ethanol or isopropanol are added drop by drop to said phosphonic acid solution at a temperature between 40° C. to 60° C. while stirring vigorously. Thereafter, the reaction mixture is kept at the boiling temperature for about one hour. After acidifying the reaction solution, treating it with a cation exchange agent, and concentrating by evaporation the reaction solution, the N-(1-sulfo hexane)-1-amino ethane-1,1-diphosphonic acid is obtained.

Yield: 89.2% of the theoretical yield.
Analysis:
Found: N: 3,9%, P: 16.3%, S: 8.9%. Calculated: N: 3.79%, P: 16.78%, S: 8,68%.

EXAMPLE 6

The procedure is the same as described in Example 5, whereby, however, 68 g. of 1,3-dodecane sultone are used in place of 1,3-hexane sultone. Yield of the resulting N-(1-sulfo dodecane)-1-amino ethane-1,1-diphosphonic acid: 87.3% of the theoretical yield.

Analysis:
Found: N: 3,4%, P: 13.2%, S: 7.6%. Calculated: N: 3.09%, P: 13.66%, S: 7.07%.

EXAMPLE 7

47.8 g. of amino methane diphosphonic acid are suspended in 100 cc. of water and 112 g. of a 50% potassium hydroxide solution are added thereto. 65 g. of 1,4-undecane sultone, dissolved in 80 cc. of methanol, are added drop by drop thereto while stirring vigorously. Thereby, the temperature slowly increases to 80° C. The reaction mixture is kept at said temperature for 30 minutes. The pH of the resulting solution is adjusted to a pH of 3.0 to 4.0. Any precipitated unreacted amino methane disphosphonic acid is filtered off and the filtrate is treated with a cation exchange agent. After evaporating the resulting solution to dryness in a waterjet vacuum, 78 g. of N-(1-sulfo undecane) amino methane diphosphonic acid are obtained.

Analysis:
Found: N: 3.1%, P: 14.1%, S: 7.7%. Calculated: N: 3,29%, P: 14.56%, S: 7.54%.

EXAMPLE 8

The procedure is the same as described in Example 7 whereby, however, 75 g. of 1,4-tetradecane sultone are added as sultone reactant in place of 65 g. of 1,4-undecane sultone. 83 g. of N-(1-sulfo tetradecane) amino methane diphosphonic acid are obtained.

Analysis:
Found: N: 3.2%, P: 12.9%, S: 7.1%. Calculated: N: 3.00%, P: 13.25%, S: 6.86%.

EXAMPLE 9

66.8 g. of phenyl amino methane diphosphonic acid and 50 g. of sodium hydroxide are dissolved in 300 cc. of water. 32 g. of 1,3-propane sultone dissolved in 75 cc. of ethanol or isopropanol, are added drop by drop thereto and the mixture is heated as described hereinabove in the preceding examples. Any unreacted phenyl amino methane diphosphonic acid is precipitated by acidifying with dilute hydrochloric acid. After filtration, a solution of the sodium salt of the corresponding N-(sulfo propane) phenyl amino methane diphosphonic acid is obtained. A sample of said solution is treated with a cation exchange agent and yields, on evaporation to dryness, the N-(sulfo propane) phenyl amino methane diphosphonic acid.

Analysis:
Found: C: 31.4%, N: 3.4%, P: 15.4%, S: 8.7%. Calculated: C: 30.85%, N: 3.60%, P: 15.91%, S: 8.24%.

EXAMPLE 10

The procedure is the same as described in the preceding example whereby, however, 36 g. of butane sultone are added as the sultone reactant in place of 1,3-propane sultone. A solution of the sodium salt of the corresponding N-(sulfo butane) phenyl amino methane diphosphonic acid is obtained.

EXAMPLE 11

On reacting a solution of 51 g. of 1-amino ethane-1,1-diphosphonic acid and 70 g. of potassium hydroxide in 300 cc. of water with a solution of 33 g. of 1,3-propane sultone in 50 cc. of methanol, a solution of the potassium salt of N-(3-sulfo propane)-1-amino ethane-1,1-diphosphonic acid is obtained. After treating said solution with a cation exchange agent, evaporating the treated solution to dryness, and washing the residue with mthanol, the corresponding N-(3-sulfo propane)-1-amino ethane 1,1-diphosphonic acid is obtained.

Yield: 90.3% of the theoretical yield. Analysis:
Found: C: 18.9%, N: 4.4%, P: 18.4%, S: 10.3%. Calculated: C: 18.35%, N: 4.28%, P: 18.93%, S: 9.80%.

The following Table illustrates the preparation of other N-(sulfo alkane) amino alkane phosphonic acids which can be produced according to the preceding example. In said Table there are mentioned the phosphonate and sulfonate reactants and the resulting reaction products and the method and example according to which the reaction products are obtained.

| Example | Phosphonate Reactant | Sultone Reactant | Reaction Product | Prepared According to Example No. |
|---|---|---|---|---|
| 12 | Amino methane diphosphonate | 1,3-Heptadecane sultone | N-(sulfo heptadecane) amino methane diphosphonic acid | 1 |
| 13 | Amino methane diphosphonate | 3-methyl-2,4-heptane sultone | N-(sulfo-3-methyl heptane) amino methane diphosphonic acid | 3 |
| 14 | Amino methane diphosphonate | 2,2-dimethyl-1,3-hexane sultone | N-(sulfo-2,2-dimethyl hexane) amino methane diphosphonic acid | 3 |
| 15 | N-methyl amino methane diphosphonate | 1,3-propane sultone | N-methyl-N-(sulfo propane) amino methane diphosphonic acid | 1 |

| Example | Phosphonate Reactant | Sultone Reactant | Reaction Product | Prepared According to Example No. |
|---|---|---|---|---|
| 16 | Imino bis-(methane phosphonate) | 1,3-butane sultone | N-(sulfo butane) imino bis-(methane phosphonic acid) | 3 |
| 17 | 1-Amino propane-1,1-diphosphonate | 1,3-propane sultone | N-(sulfo propane)-1-amino propane-1,1-diphosphonic acid | 1 |
| 18 | 2-Carboxy-1-amino ethane-1,1-disphosphonate | 1,3-butane sultone | N-(sulfo butane)-2-carboxy-1-amino ethane-1,1-diphosphonic acid | 4 |
| 19 | 1-Amino propane-1,1,3-triphosphonate | 1,4-butane sultone | N-(sulfo butane)-1-amino propane-1,1,3-triphosphonic acid | 3 |

Compounds in which the substituent $R_1$ together with the substituent $R_3$ is alkylene with 3 to 5 carbon atoms and thus forms an azacycloalkane ring with the group

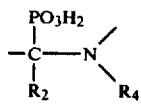

are also obtained according to the processes described hereinabove and in the examples. Thus, for instance, azacycloheptane-2,2-diphosphonic acid yields by reaction, for instance, with 1,3-propane sultone, as described hereinabove, the corresponding N-(sulfo propane) azacycloheptane diphosphonic acid. Other N-(sulfo alkane) azacycloalkane phosphonic acids are produced in a corresponding manner.

Of course, many changes and variations in the reactants used and the reaction conditions, duration, temperature, and pressure, in the manner in which the reaction solution is worked up, purified, and converted to the N-sulfo alkane amino alkane phosphonic acid or its alkali metal salts and the like may be made by those skilled in the art in accordance with the principles set forth herein and in the claims annexed thereto.

Preferably strongly acid cation exchange agents such as, for instance, sulfonated polymerization products of styrene, divinylbenzene, and the like, are used for producing the free sulfo alkane amino alkane phosphonic acids of the present invention, for instance, sulfonated polymers of styrene or divinylbenzene as they are known under the trademark "Duolite C25" of the firm Diamond Alkali Co., "Amberlite IR 112 and IR 120" of the firm Rohm & Haas Co., "Dowex 50" of the firm Dow Chemical Co., "Levatit S100" of the firm Bayer A. G., and others.

The novel N-(sulfo alkane) amino alkane phosphonic acids and their alkali metal salts as well as their reaction solutions or the mother liquors obtained after separating the unreacted crystalline phosphonic acids are used, as stated above, as additives to aqueous media to eliminate or suppress the disturbing and obnoxious effects of hardness-forming agents present therein or to exclude the action of polyvalent metal ions in said media. On account of their high sequestering power they can advantageously be used for preventing scale and deposit formation in aqueous systems and thus are advantageously employed, for instance, in textile bleaching baths, in water used for sterilizing cans, for preventing formation of resinous deposits in the manufacture of paper, and the like.

The phosphonic acids according to the present invention can also be used as sequestering, complexing, and/or chelating agents for other purposes, for instance, as described in U.S. Pat. No. 3,860,391 in peroxide bleaching baths, and in U.S. Pat. Nos. 3,833,517 and 3,954,401 in baths for the treatment of cellulose fiber materials and for other uses for which phosphonic acids have been used heretofore. If desired, the alkali metal or ammonium salts or the salts with organic amines or solutions thereof can also be used in place of the free acids. The salts can be prepared, for instance, by neutralizing the acids with the calculated amounts of alkali metal hydroxides, ammonia, or organic amines.

The following examples illustrate the manner in which the sulfo alkane amino alkane phosphonic acids according to the present invention can be employed without, however, limiting their usefulness to these examples.

EXAMPLE 20

The following test was carried out in an upright autoclave of a capacity of 10 liters of water. The autoclave was operated at about 4 atmospheres gauge and at a temperature of 140° C. The autoclave was charged with conventional tin plated cans.

Tap water of the following composition was used for sterilization:

| Total degree of hardness | 25° German hardness |
|---|---|
| Hardness due to carbonates | 17° German hardness |
| Chlorides | 53 mg./l. |
| Sulfates | 85 mg./l. |
| Free carbon dioxide | 40 mg./l. |
| Bound carbon dioxide | 125 mg./l. |
| pH-value | 7.2 |

Before sterilization of the cans 5 cc. of a 30% solution of N-(sulfo propane)-1-amino ethane-1,1- diphosphonic acid were added to the water. Addition of said phosphonic acid resulted in keeping not only the sterilized cans but also the autoclave free of incrustations. The cans had a glossy and shiny appearance.

EXAMPLE 21

250 g. of bleached sulfite pulp known for its property of causing continuously difficulty on the paper machine due to resin deposition were beaten to a 3% suspension in water. The resulting shock suspension was ground in a Hollander beater to about 78° Schopper-Riegler, i.e. so as to form a well beaten pulp suitable for producing dense sheets of parchment-like paper. The pH-value of the resulting slurry was 6.0. Before starting beating, 0.5 kg. of the tetrasodium salt of N-(sulfo propane)-2-carboxy-1-amino ethane-1,1-diphosphonic acid were added to the slurry in the Hollander beater. After beating and refining, 0.8 kg. of the same phosphonic acid were admixed thereto.

When proceeding in this manner, no resinous deposits were observed on the walls of the Hollander beater and also not on the pipe lines and subsequently on the paper machine.

EXAMPLE 22

Treatment of water used for sterilization of cans.

Tin plated cans are placed into a 10 liter autoclave. Tap water of the following composition is used for sterilization of the cans:

| Total hardness | 25° German hardness |
|---|---|
| Carbonate hardness | 17° German hardness |
| Chlorides | 53 mg./l. |
| Sulfates | 85 mg./l. |
| Free Carbon dioxide | 40 mg./l. |
| Bound carbon dioxide | 125 mg./l. |
| pH-value | 7.2 |

0,25 g./l. of N-(sulfo propane)-1-amino ethane-1,1-diphosphonic acid are added to the tap water. Sterilization is effected by heating to 140° C. at about 4 atmospheres gauge. Addition of the phosphonic acid compound inhibits scale and deposit formation on the sterilized cans as well as on the walls of the autoclave.

The same or similar results as described in Examples 20 to 22 were observed when using other N-sulfo alkane amino alkane phosphonic acids as obtained, for instance, according to Examples 1 to 19.

We claim:

1. A compound of the formula $$\begin{array}{c} PO_3H_2 \\ | \\ R_1-C-N \\ | \\ PO_3H_2 \end{array} \begin{array}{c} R_3 \\ \diagdown \\ \diagup \\ R_4 \end{array}$$

$R_1$ being hydrogen, methyl or a carboxy lower alkylene group;

$R_3$ being hydrogen or methyl; and $R_4$ being an alkylene sulfonic acid group of the Formula $C_nH_{2n}SO_3H$ and n equals 1–14 or 17 wherein $R_1$ is a carboxy alkylene group or $R_3$ is methyl or n equals 12–14 or 17;

and the water-soluble salts thereof.

2. A compound according to claim 1 wherein $R_1$ is a carboxy lower alkylene group.

3. N-(sulfo butane)-2-carboxy-1-amino ethane-1,1-diphosphonic acid.

4. A compound according to claim 1 wherein $R_3$ is methyl.

5. N-methyl-N-(sulfo propane) amino methane diphosphonic acid.

6. A compound according to claim 1 wherein n is 12–14 or 17.

7. N-(sulfo dodecane)-1-amino ethane-1,1-diphosphonic acid.

8. N-(sulfo tetradecane) amino methane diphosphonic acid.

9. N-(sulfo heptadecane) amino methane diphosphonic acid.

* * * * *